(12) United States Patent
Lai et al.

(10) Patent No.: US 7,014,460 B2
(45) Date of Patent: Mar. 21, 2006

(54) ORTHODONTIC APPLIANCE WITH FATIGUE-RESISTANT ARCHWIRE RETAINING LATCH

(75) Inventors: Ming-Lai Lai, Arcadia, CA (US); Jirina V. Pospisil, Hacienda Heights, CA (US)

(73) Assignee: 3M Innovative Properties Company, St. Paul, MN (US)

( * ) Notice: Subject to any disclaimer, the term of this patent is extended or adjusted under 35 U.S.C. 154(b) by 332 days.

(21) Appl. No.: 10/287,089

(22) Filed: Nov. 4, 2002

(65) Prior Publication Data

US 2004/0086825 A1    May 6, 2004

(51) Int. Cl.
*A61C 3/00*    (2006.01)
(52) U.S. Cl. .................. 433/11; 433/8; 433/10
(58) Field of Classification Search .................. 433/10, 433/11, 12, 13, 14, 15, 8
See application file for complete search history.

(56) References Cited

U.S. PATENT DOCUMENTS

| | | |
|---|---|---|
| 1,991,047 A | 2/1935 | Boyd et al. |
| 3,052,027 A | 9/1962 | Wallshein |
| 3,084,437 A | 4/1963 | Neger |
| 3,327,393 A | 6/1967 | Brader |
| 3,464,112 A | 9/1969 | Silverman et al. |
| 3,464,113 A | 9/1969 | Silverman et al. |
| 3,724,074 A | 4/1973 | Wallshein |
| 3,772,787 A | 11/1973 | Hanson |
| 4,103,423 A | 8/1978 | Kessel |
| 4,149,314 A | 4/1979 | Nonnenmann |
| 4,171,568 A | 10/1979 | Forster |
| 4,197,642 A | 4/1980 | Wallshein |
| 4,248,588 A | 2/1981 | Hanson |
| 4,260,375 A | 4/1981 | Wallshein |
| 4,371,337 A | 2/1983 | Pletcher |
| 4,492,573 A | 1/1985 | Hanson |
| 4,496,318 A | 1/1985 | Connelly, Jr. |
| 4,551,094 A | 11/1985 | Kesling |
| 4,559,012 A | 12/1985 | Pletcher |
| 4,698,017 A | 10/1987 | Hanson |
| 4,712,999 A | 12/1987 | Rosenberg |
| 4,725,229 A | 2/1988 | Miller |
| 4,846,681 A | 7/1989 | Mourany et al. |
| 5,039,302 A | 8/1991 | Keys |
| 5,094,614 A | 3/1992 | Wildman |
| 5,269,681 A | 12/1993 | Degnan |
| 5,322,435 A | 6/1994 | Pletcher |

(Continued)

FOREIGN PATENT DOCUMENTS

EP    1090604    4/2001

(Continued)

OTHER PUBLICATIONS

Voudouris, John C. "Seven Clinical Principles of Interactive Twin Mechanisms", *Journal Clinical Orthodontics, Inc.* 1997, vol. XXXI, No. 1, pp. 55-65.

*Primary Examiner*—Kevin Shaver
*Assistant Examiner*—Candice C. Stokes
(74) *Attorney, Agent, or Firm*—James D. Christoff (57) ABSTRACT

An orthodontic appliance such as a bracket or buccal tube has a latch for retaining an archwire in an archwire slot. The latch releases the archwire from the archwire slot whenever the archwire exerts a force on the appliance that exceeds a certain minimum value. The latch comprises at least one clip having certain features that significantly reduce strain during opening movements of the clip, so that the likelihood of fracture of the clip during use is significantly reduced.

26 Claims, 3 Drawing Sheets

U.S. PATENT DOCUMENTS

| | | | |
|---|---|---|---|
| 5,356,289 A | 10/1994 | Watanabe | |
| 5,358,402 A | 10/1994 | Reed et al. | |
| 5,366,372 A | 11/1994 | Hansen et al. | |
| 5,380,196 A | 1/1995 | Kelly et al. | |
| 5,439,379 A | 8/1995 | Hansen | |
| 5,466,151 A | 11/1995 | Damon | |
| 5,474,445 A | 12/1995 | Voudouris | |
| 5,516,284 A | 5/1996 | Wildman | |
| 5,562,444 A | 10/1996 | Heiser et al. | |
| 5,613,850 A | 3/1997 | Wildman et al. | |
| 5,630,715 A | 5/1997 | Voudouris | |
| 5,630,716 A | 5/1997 | Hanson | |
| 5,685,711 A | 11/1997 | Hanson | |
| 5,711,666 A | 1/1998 | Hanson | |
| 5,857,849 A | 1/1999 | Kurz | |
| 5,857,850 A | 1/1999 | Voudouris | |
| 5,863,199 A | 1/1999 | Wildman | |
| 5,890,893 A | 4/1999 | Heiser | |
| 5,908,293 A | 6/1999 | Voudouris | |
| 5,913,680 A | 6/1999 | Voudouris | |
| 5,967,773 A | 10/1999 | Roman et al. | |
| 5,971,753 A | 10/1999 | Heiser | |
| 6,168,428 B1 | 1/2001 | Voudouris | |
| 6,554,612 B1 * | 4/2003 | Georgakis et al. | 433/11 |
| 2001/0029008 A1 | 10/2001 | Jordan et al. | |

FOREIGN PATENT DOCUMENTS

| | | |
|---|---|---|
| WO | WO 97/41795 | 11/1997 |
| WO | WO 98/20805 | 5/1998 |
| WO | WO 01/22901 | 4/2001 |
| WO | WO 02/089693 | 11/2002 |

\* cited by examiner

ORTHODONTIC APPLIANCE WITH FATIGUE-RESISTANT ARCHWIRE RETAINING LATCH

BACKGROUND OF THE INVENTION

1. Field of the Invention

This invention broadly relates to appliances that are used during the course of orthodontic treatment. More particularly, the present invention relates to an orthodontic appliance such as a bracket or molar appliance having an improved latch that releasably retains an archwire in an archwire slot of the appliance.

2. Description of the Related Art

Orthodontic therapy is a specialized type of treatment within the field of dentistry, and involves movement of malpositioned teeth to orthodontically correct locations. Orthodontic treatment often improves the patient's occlusion and typically enhances the aesthetic appearance of the teeth.

Many types of orthodontic treatment programs involve the use of a set of tiny appliances and wires that are commonly known collectively as "braces". During such treatment programs, small appliances known as brackets are fixed to the patient's anterior, cuspid and bicuspid teeth, and an archwire is inserted into a slot of each bracket. The archwire forms a track to guide movement of the teeth to orthodontically correct locations. End sections of the archwires are typically captured in tiny appliances known as buccal tubes that are fixed to the patient's molar teeth.

Many types of orthodontic brackets have archwire slots that are open on one side for insertion of the archwire, and bounded on remaining sides by walls or other structure. Brackets that are intended to be bonded to the patient's front tooth surfaces often have archwire slots that are open either on a buccolabial side (i.e., a side facing the patient's cheeks or lips) or an occlusal side (i.e., a side facing the outer tips of the teeth) of the archwire slot. Some brackets, however, are intended to be fixed to the lingual side of the patient's teeth (i.e., the side of the teeth facing the patient's tongue) and typically have an archwire slot that is open on a lingual side or on an occlusal side.

Many orthodontists use ligatures to connect the archwire to the brackets and to urge the archwire into an orientation of seating engagement in the archwire slot. One type of commercially available orthodontic ligature is a small, elastomeric O-ring. Orthodontic O-ring ligatures are installed by stretching the O-ring around small wings (known as "tiewings") that are connected to the bracket body on the gingival side (i.e., the side facing the patient's gingiva or gums) and on the occlusal side of the archwire slot. Once installed, the O-ring ligature extends around the back or lingual side of the tiewings as well as over the labial side of the archwire and urges the archwire toward a fully seated position in contact with a lingual wall of the archwire slot.

Metal ligatures, such as ligatures made of stainless steel, are also used to retain archwires in archwire slots of brackets. Metal ligatures are typically made of a short section of initially straight wire that is subsequently formed into a loop. During installation, the wire ligature is hooked around the tiewings and extended over the labial side of the archwire. End sections of the ligature are then twisted together to close the loop and retain the ligature in place.

Unfortunately, some orthodontists are not entirely satisfied with elastomeric and metal ligatures. Such ligatures are somewhat time-consuming to install, both during initial installation and also during reinstallation whenever replacement of the archwire or ligatures is desired. As can be appreciated, decreasing the amount of time needed for ligation can help to reduce the total time that the practitioner must spend with the patient and consequently decrease the overall costs of orthodontic treatment.

Other disadvantages are also associated with elastomeric and metal ligatures. For example, there have been reports that certain polyurethane elastomeric ligatures have exhibited deformation and force decay during the course of treatment. In some instances, elastomeric ligatures are stained by food and beverages consumed by the patient and become somewhat unsightly. Metal ligatures often have sharp ends that may retain plaque and food debris and also may increase the risk of infection.

In an effort to overcome the problems associated with conventional ligatures, a variety of orthodontic brackets have been proposed having various types of latches for coupling the archwire to the bracket. Such brackets are also known as self-ligating brackets. The latch comprises a movable clip, spring member, cover, shutter, bail or other structure that is connected to the bracket body for retaining an archwire in the archwire slot.

Examples of self-ligating orthodontic brackets having generally U-shaped ligating latch clips are described in U.S. Pat. Nos. 3,772,787, 4,248,588 and 4,492,573. In general, the clip of such brackets is slidably mounted on the bracket body, and a dental explorer or other small-tipped dental tool is used to move the clip relative to the body when needed in order to open or close the archwire slot. A self-ligating bracket known as the "Speed" brand bracket also has a movable, generally U-shaped clip for ligating the archwire to the bracket.

Other types of self-ligating brackets have latches that resemble swinging shutters or closures that pivotally move between a slot-open and a slot-closed position. For example, the bracket illustrated in U.S. Pat. No. 4,712,999 has a rotatable cover plate that is pivotally connected at one end to a tiewing of the bracket along one side of the slot, and is releasably engagable at the other end with a tiewing that is located along the opposite side of the archwire slot. Other orthodontic brackets with swinging latches are described in U.S. Pat. Nos. 4,103,423, 5,516,284 and 5,685,711.

U.S. Pat. Nos. 4,371,337 and 4,559,012 describe self-ligating orthodontic brackets having latches that rotate about the longitudinal axis of the archwire slot. The latch of these references has a somewhat cylindrical shape and is rotatably received in a mating, cylindrical channel, and an outwardly extending arm is provided to assist in rotatably moving the latch between a slot-open and a slot-closed position.

A self-ligating orthodontic bracket that is described in U.S. Pat. No. 5,711,666 has a latch that comprises a flexible flat spring member. One end of the spring member is fixed to the bracket body on one side of the archwire slot, and the opposite end of the spring member has notches that releasably engage latch sears or catches when the spring member is moved to a slot-closed position. To open the slot, the notches are disengaged from the catches and the spring member is bent to an orientation sufficient to enable the archwire to be removed from the archwire slot.

Other types of self-ligating orthodontic brackets have latches that comprise essentially flat plates that are slidable between a slot-open and a slot-closed position. Examples of such construction are shown in U.S. Pat. Nos. 5,094,614, 5,322,435 and 5,613,850. In general, the sliding latches described in those references move in upright channels that are located buccolabially of the archwire slot.

Another type of self-ligating bracket that has been proposed in the past has a latch that is made of a section of wire material that functions similar to a bail. The orthodontic brackets described in U.S. Pat. Nos. 4,149,314, 4,725,229 and 5,269,681 have wire-like latches that swing between a slot-closed position and a slot-open position. The orthodontic bracket described in U.S. Pat. No. 4,260,375 has a wire latch that is slidable between a slot-open and a slot-closed position.

Improved self-ligating orthodontic brackets are described in two pending PCT applications entitled "ORTHODONTIC APPLIANCE WITH SELF-RELEASING LATCH", WO01/22901 and US02/09896. The appliances described in these applications have a latch for retaining an archwire in the archwire slot, and the latch releases the archwire from the archwire slot whenever the archwire exerts a force on the appliance that exceeds a certain minimum value. The minimum value is significantly less than the force required in the same direction to debond the appliance from the tooth, and consequently helps ensure that the appliance will not spontaneously debond from the tooth during the course of treatment.

In certain embodiments of the appliances described in the PCT applications mentioned above, the archwire may be inserted into the archwire slot by pressing the archwire against the latch. The latch is constructed to self-open without the need for hand instruments or other tools. Consequently, such appliances are a great advantage to the practitioner in that the time needed for connecting the archwire to the appliance can be significantly reduced.

While the appliances described in the above-mentioned PCT applications represent a significant advance in orthodontic appliance technology, there is a continuing need to improve the state of the art relating to self-ligating appliances. One improvement that would be desirable relates to improvements to the latch that could help assure the latch reliably opens and closes as intended over extended periods of time. In addition, it is important to assure that the latch does not fracture during use so that the appliance need not be replaced.

Unfortunately, one problem associated with improving the latches described above relates to their inherently small size. For example, some of the latches described in the above-referenced PCT applications may have overall sizes of less than about 2.5 mm×1.6 mm×0.3 mm. While it is possible to increase the size of the latch in order to increase its fatigue life, such a modification is not desirable because the overall size of the appliance is likely to be correspondingly increased. Increasing the size of the appliance is generally not satisfactory because of the increased likelihood that the appliance will impinge on adjacent soft tissue and cause pain to the patient. In addition, an increase in appliance size will usually cause the appliance to be more visible in the oral cavity and adversely affect its aesthetic appearance.

SUMMARY OF THE INVENTION

The present invention is directed toward improvements in self-ligating orthodontic appliances. In one aspect of the invention, the appliances have an improved latch that comprises one or more clips. The clips are provided with certain features that help assure that the latch will reliably and consistently function as intended for extended periods of time even after the latch has been opened and closed a number of times.

In more detail, the present invention in one embodiment is directed to a clip for releasably retaining an archwire in an archwire slot of an orthodontic appliance. The clip comprises a first section and a second section opposed to the first section. The first section and the second sections are spaced apart from each other to present a region for receiving an archwire. A third section extends in a certain direction and interconnects the first and second sections. A first arm portion is connected to the first section remote from the third section, and a second arm portion is connected to the second section remote from the third section. The first and second sections are movable toward and away from each other for enabling the arm portions to retain and release an archwire in the region between the first section and the second section respectively. The first section decreases in width as the first arm portion is approached, and the second section decreases in width as the second arm portion is approached.

Another embodiment of the invention is directed to a clip for releasably retaining an archwire in an archwire slot of an orthodontic bracket. The clip comprises a first section and a second section opposed to the first section. The first section and the second section are spaced apart from each other to present a region for receiving an archwire. A third section extends in a certain direction and interconnects the first section and the second section. A first arm portion is connected to the first section remote from the third section. A second arm portion is connected to the second section remote from the third section. The arm portions are movable toward and away from each other for retaining and releasing an archwire in the region between the first section and the second section. A recess is provided adjacent the third section and communicates with the archwire-receiving region. The recess is smaller than the region in directions parallel to said certain direction.

In another embodiment, the present invention is directed to a latch for releasably retaining an archwire in an archwire slot of an orthodontic appliance. The latch has a longitudinal axis that generally extends along a buccolabial-lingual reference axis. The latch includes at least one section having a mesial wall, a distal wall, an occlusal wall and a gingival wall. The mesial wall and the distal wall are oriented at an angle other than ninety degrees relative to the occlusal wall and the gingival wall.

Additional embodiments of the invention are directed toward orthodontic appliances that include at least one clip as mentioned in either of the preceding paragraphs.

Other aspects of the invention are described in the paragraphs that follow and are illustrated in the accompanying drawings.

DETAILED DESCRIPTION OF THE PREFERRED EMBODIMENTS

Figure 1:
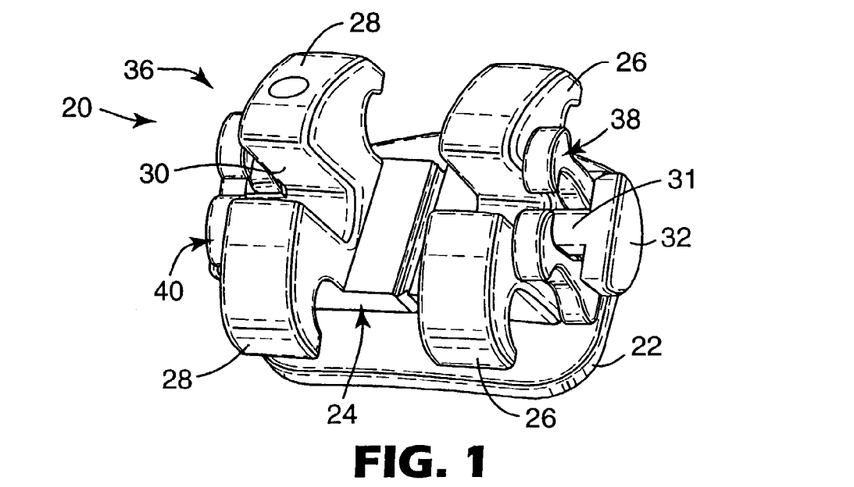
FIG. 1 is a perspective view of an orthodontic appliance having a latch in accordance with one embodiment of the present invention.
Figures 2, 3:
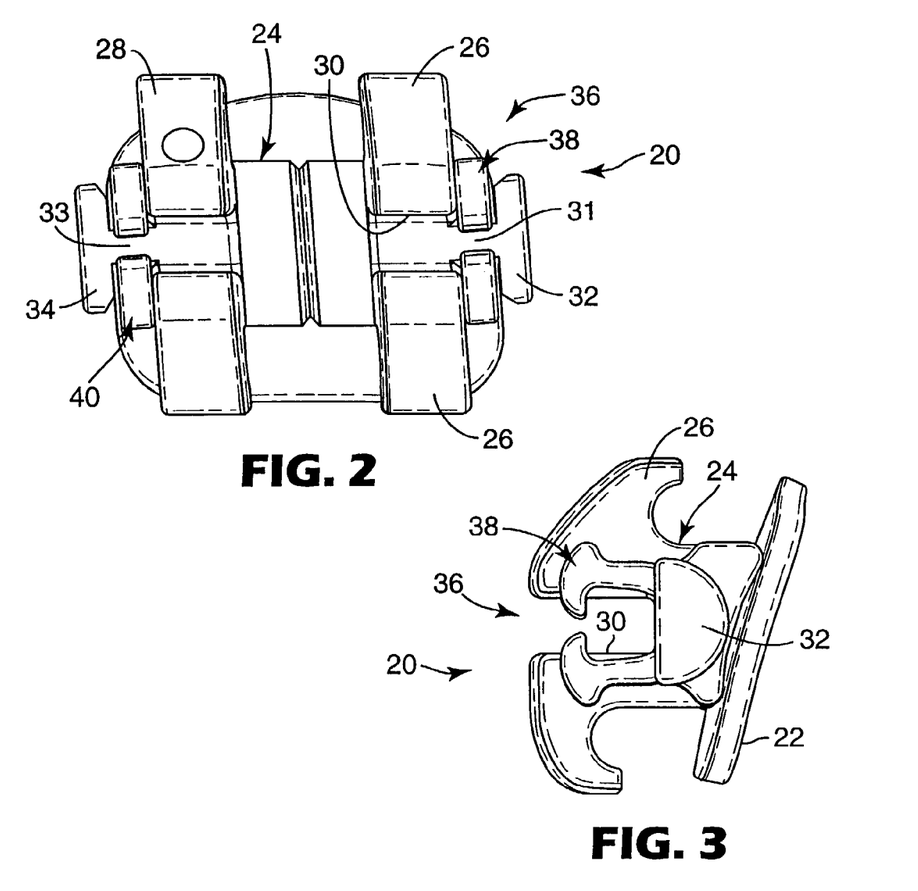
FIG. 2 is a front elevational view of the appliance shown in FIG. 1, looking in a lingual direction toward the appliance.
FIG. 3 is a side elevational view looking in a distal direction toward the appliance illustrated in FIGS. 1 and 2.

An orthodontic appliance constructed in accordance with one embodiment of the present invention is illustrated in FIGS. 1–3 and is broadly designated by the numeral 20. The appliance 20 in this instance is an orthodontic bracket adapted to be secured to the buccolabial surface of a patient's tooth. Alternatively, the appliance could be a molar appliance or any other orthodontic appliance that is adapted to receive an archwire for controlling movement of the teeth during the course of orthodontic therapy.

The appliance 20 includes a base 22 for bonding the appliance 20 directly to the patient's tooth enamel by use of an adhesive. Preferably, the base 22 has an outwardly-facing concave compound contour that matches the convex compound contour of the patient's tooth surface. Optionally, the base 22 may be provided with grooves, particles, recesses, undercuts, a chemical bond enhancement material or any other material or structure or any combination of the foregoing that facilitates bonding the appliance 20 directly to the patient's tooth surface.

A body 24 extends outwardly from the base 22 in a generally buccolabial direction. The body 24 includes a spaced-apart pair of mesial tiewings 26 and a pair of spaced-apart distal tiewings 28. An archwire slot 30 extends across the body 24 in a generally mesial-distal direction and between the space presented by the pair of mesial tiewings 26 and the space presented between the pair of distal tiewings 28. Optionally, the tiewings 26, 28 may be omitted.

The body 24 also includes a mesially extending support 31 that is connected to an outermost mesial flange 32 and a distally extending support 33 that is connected to an outermost distal flange 34. Each of the flanges 32, 34 has a somewhat semi-circular configuration in elevational view, although other shapes are also possible. Preferably, the flanges 32, 34 are integral with the supports 31, 33 respectively although as another option the flanges 32, 34 may be affixed to the remaining portions of the body 24 after first being separately manufactured.

The appliance 20 also includes a latch 36 that is connected to the body 24 for releasably retaining an archwire in the archwire slot 30. In this embodiment, the latch 36 includes a mesial clip 38 and a distal clip 40 although other alternatives are also possible. For example, the latch 36 could have only a single clip that is optionally located in the space between the pair of mesial tiewings 26 and the pair of distal tiewings 28.

Figure 4:
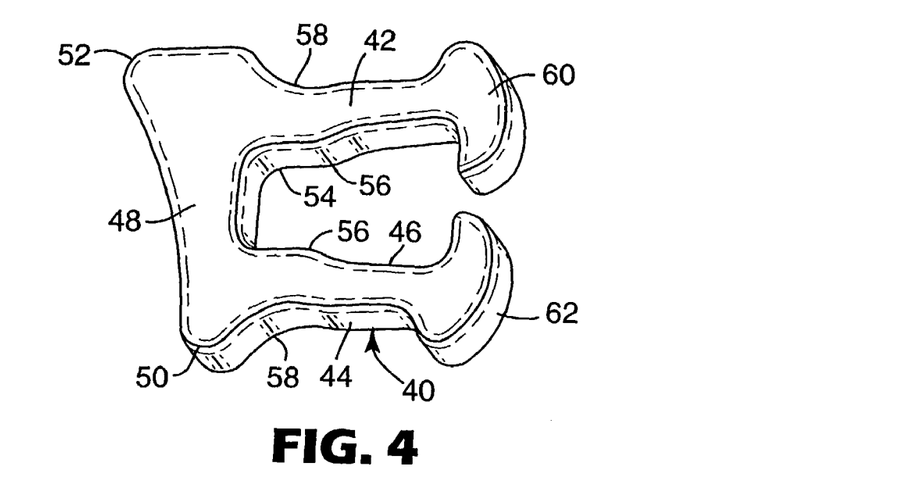
FIG. 4 is an enlarged perspective view of one of two clips that comprise the latch of the appliance depicted in FIGS. 1–3.
Figure 5:
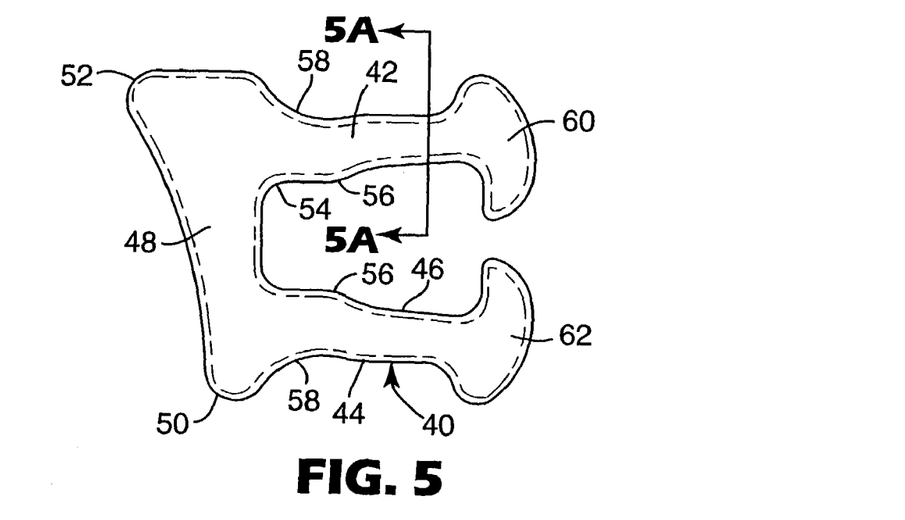
FIG. 5 is an enlarged side elevational view of the clip illustrated in FIG. 4, looking in a mesial direction.

The distal clip 40 is shown alone in FIGS. 4 and 5 and has an overall, generally "C"-shaped configuration. The distal clip 40 includes a first section 42 and a second section 44 that is opposed to the first section 42. In their normal, relaxed configuration, the first section 42 and the second section 44 extend in generally parallel directions. The first section 42 is spaced apart from the second section 44 to present a region 46 for receiving an archwire.

The clip 40 also includes a third section 48 that interconnects the first section 42 and the second section 44. When assembled to the body 24, the third section 48 extends in a generally occlusal-gingival direction along the buccolabial surface of the base 22 as can be appreciated by reference to FIG. 3. The third section 48 extends beyond the first section 42 and the second section 44 in an occlusal-gingival direction and terminates at a rounded, protruding outermost occlusal corner 50 and a rounded, protruding outermost gingival corner 52.

Preferably, and as shown in FIG. 3, the corners 50, 52 contact the buccolabial side of the base 22 when the clip 40 is assembled to the body 24. However, a middle portion of the third section 48 is slightly spaced from the buccolabial side of the base 22. Such construction ensures that the clip 40 contacts the base 22 at two locations and does not unduly rock about a mesial-distal reference axis during use.

The clip 40 also includes a recess 54 that communicates with the archwire-receiving region 46. The recess 54 is smaller than the region 46 in directions parallel to the direction of extension of the third section 48, which in turn is generally parallel to an occlusal-gingival reference axis. At the entrance to the recess 54, the first and second sections 42, 44 present a pair of opposed protrusions 56 that extend inwardly toward each other. The opposite side of the first and second sections 42, 44 also each present a notch 58 that is opposed to the respective, adjacent protrusion 56.

The clip 40 also has a pair of arm portions 60, 62 that extend inwardly toward each other. A buccolabial edge of the arm portions 60, 62 is smoothly curved in an arc about a mesial-distal reference axis. For the arm portion 60, this smooth outer curve extends in a gingival direction beyond the gingival side of the first section 42. For the arm portion 62, the smooth outer curve extends in an occlusal direction beyond the occlusal side of the second section 44.

The clip 40 is shown in its normal, relaxed orientation in FIGS. 1–5. However, the arm portions 60, 62 are movable away from each other in order to admit an archwire into the archwire-receiving region 46 when desired. To this end, the first and second sections 42, 44 bend in respective arcs away from each other in order to enable the arm portions 60, 62 to move apart from each other.

The smooth, outer curve on the buccolabial side of the arm portions 60, 62 enables the clip 40 to open and admit an archwire into the region 46 by pressing an archwire against the outer curved edges of the arm portions 60, 62. As pressure is exerted on the curved edges by the archwire, the first and second sections 42, 44 deflect away from each other in order to admit the archwire into the region 46. Once the archwire is received in the region 46, the inherent resiliency of the clip 40, and particularly the resiliency of the first and second sections 42, 44, enables the arm portions 60, 62 to spring back toward each other and to their normal, relaxed configuration as shown in the drawings in order to retain the archwire in the archwire slot 30.

Figure 5A:
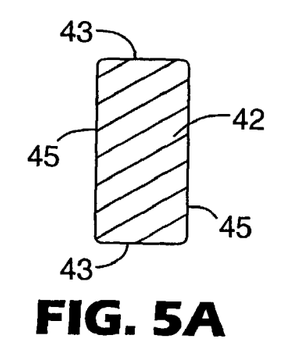
FIG. 5a is an enlarged cross-sectional view of the clip taken along lines 5a—5a of FIG. 5, except that portions of the clip in the background have been omitted.

FIG. 5a is a cross-sectional view of the first section 42 of the clip 40. As shown, the shape of this cross-section is rectangular. The first section 42 has a longitudinal axis extending generally along a buccolabial-lingual reference axis, and includes occlusal and gingival walls 43 as well as mesial and distal walls 45. The walls 43, 45 are substantially perpendicular to each other as is preferred for appliances having a zero angulation. A similar orientation of walls is present in other regions of the clip 40, including the second and third sections 44, 48 as well as in the arm portions 60, 62. Although not shown in the drawings, the intersections between the walls are rounded.

Figure 5B:
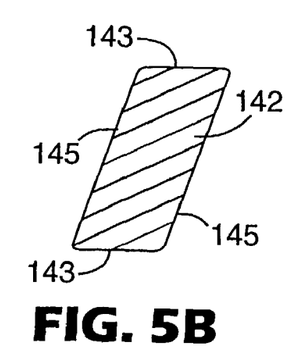
FIG. 5b is a view somewhat similar to FIG. 5a but showing a clip according to another embodiment of the invention.

FIG. 5b is a view somewhat similar to FIG. 5a, but showing a section of a clip 140 according to another embodiment of the invention. The clip 140 has a shape, when viewed in a mesial or distal direction, that is similar to the shape of the clip 40. However, in this embodiment, a first section 142 of the clip 140 has occlusal and gingival walls 143 that are oriented at an angle other than 90 degrees relative to mesial and distal walls 145. A similar orientation of walls is present at other regions of the clip 140, including in a second and third section as well as in arm portions of the clip.

The cross-sectional shape of the clip 140 resembles a rhomboid or a parallelogram having no right angles. Such construction is a particular advantage when used in combination with appliances known as "angulated" appliances having an archwire slot that extends at a similar angle relative to mesial and distal sides of tiewings and/or the appliance body. In these instances, the total area occupied by a clip may remain the same without unduly decreasing its cross-sectional area or its resultant strength and fatigue life.

To assemble the clip 40 to remaining components of the appliance 20, the clip 40 is preferably put in place before the base 22 is affixed to the body 24. During assembly, the clip 40 is moved in a buccolabial direction in the space between the distal flange 34 and the remaining portions of the body 24 and the arm portions 60, 62 are spread apart a distance sufficient to enable the support 33 to be received in the region 46. The clip 40 is then moved further in a buccolabial direction until such time as the support 33 is received in the recess 54.

Next, and after the clip 38 is installed in a similar manner, the base 22 is affixed to the body 24 by a suitable process such as brazing or welding (including laser welding). Once the base 22 is affixed to the body 24, the clip 40, and particularly the third section 48, is captured between the support 33 and the base 22 and is thereafter retained in place. At this time, the region 46 is aligned with the archwire slot 30 as can be appreciated by comparison of FIG. 2 and FIG. 3.

The clip 40 (including the first and second sections 42, 44) is sufficiently stiff to retain the archwire in the archwire slot 30 during the course of treatment so long as the forces exerted by the archwire on the appliance 20 are below a certain minimum value in a generally buccolabial direction (more particularly, in a direction opposite to the direction of insertion of the archwire into the archwire slot 30). However, whenever the forces exerted by the archwire on the appliance 20 in the same direction are greater than the minimum value, as might occur when unexpectedly high forces are encountered, the first and second sections 42, 44 deflect outwardly and the arm portions 60, 62 move apart from each other to open the clip 38 and enable the archwire to be released from the archwire slot 30. Further details regarding such forces are described in the aforementioned PCT applications entitled "ORTHODONTIC APPLIANCE WITH SELF-RELEASING LATCH", WO01/22901 and US02/09896, both of which are expressly incorporated by reference herein.

Preferably, the clip 38 is identical to the clip 40. The latch 36, comprising the clips 38, 40, preferably releases the archwire from the archwire slot 30 in a generally buccolabial direction whenever the archwire exerts a force in the same direction on the appliance 20 that is in the range of about 0.2 lb (0.1 kg) to about 11 lb (5 kg), more preferably in the range of about 0.4 lb (0.2 kg) to about 5.5 lb (2.5 kg), and most preferably in the range of about 0.75 lb (0.34 kg) to about 3.0 lb (1.4 kg). Preferably, the minimum value is sufficiently high to prevent the archwire from unintentionally releasing from the archwire slot 30 during the normal course of orthodontic treatment. As such, the archwire can exert forces on the appliance 20 sufficient to carry out the treatment program and move the associated teeth as desired.

Preferably, the minimum value for self-release (i.e., self-opening) of the latch 36 is substantially less than the force required in the same direction to debond the appliance 20 from the associated tooth. The minimum value for self-release of the latch 36 is preferably less than about one-half of the force required in the same direction to debond the appliance 20 from the associated tooth. For example, if the expected bond strength of the adhesive bond between the appliance 20 and the associated tooth is 16 lbs (7.2 kg) in a buccolabial direction, the latch 36 is constructed to self-release the archwire whenever the archwire exerts a force in the same buccolabial direction on the appliance 20 that is somewhat greater than about 8 lbs (3.6 kg).

To determine the force to release the latch 36, a section of archwire is selected having an area in longitudinally transverse sections that is complemental to (i.e., substantially fills) the cross-sectional area of the archwire slot 30. Next, a sling is constructed and is connected to the archwire section at locations closely adjacent, but not in contact with the mesial flange 32 and the distal flange 34. Optionally, the sling is welded or brazed to the archwire section. Next, the sling is pulled away from the appliance 20 while the appliance 20 is held in a stationary position, taking care to ensure that the longitudinal axis of the archwire section does not tip relative to the longitudinal axis of the archwire slot 30. The force to release the latch 36 may be determined by use of an Instron testing apparatus connected to the sling, using a crosshead speed of 0.5 in/min (1.3 cm/min). Alternatively, a shaker apparatus (such as Model 300 from APS Dynamics of Carlsbad, Calif.) may be used along with a force transducer (such as model 208C01 from PCB of Buffalo, N.Y.) to measure the force.

The self-releasing latch 36 is a benefit to the practitioner, in that the likelihood of spontaneous debonding of the appliance 20 is substantially reduced. For example, if the practitioner attempts to place a relatively large archwire in the archwire slot 30 and the latch 36 self-releases as soon as the practitioner releases the archwire, the practitioner can then use an archwire with less stiffness in its place so that the appliance 20 is not detached from the tooth surface. As another example, if the archwire is initially held in the archwire slot 36 by the arm portions 60, 62 and the archwire subsequently exerts a larger force on the appliance 20 (as may occur, for example, when the archwire encounters a hard object such as when the patient is chewing relatively hard food), the arm portions 60, 62 spread apart to their slot-open positions to release the archwire so that the appliance 20 does not debond from the tooth. Treatment can then be resumed by merely replacing the archwire in the archwire slot 30 without the need to rebond the base 22 to the associated tooth.

Preferably, the distance between the opposed ends of the arm portions 60, 62 is less than the overall occlusal-gingival dimension of the smallest archwire expected to be used during the course of treatment. The archwire need not fill the archwire slot 30 and flatly engage the wall portions defining the archwire slot 30 in all instances. For example, a somewhat smaller wire, and perhaps an archwire having a circular cross-sectional shape, may be used during a portion of the treatment program. The distance between the opposed ends of the arm portions 60, 62 is preferably selected so that a variety of archwires of different cross-sectional configurations may be used in connection with the appliance 20.

Preferably, the distal clip 40 is identical to the mesial clip 38. Optionally, however, it is possible to construct the clips 38, 40 somewhat differently to address certain circumstances. For example, if a malpositioned tooth is initially oriented such that its mesial side is rotated in a lingual direction, it may be desirable to increase the stiffness of the mesial clip 38 so that a somewhat greater force is needed to release the archwire from the archwire slot 30 in comparison to the force needed to release the archwire from the distal clip 40. Other options are also possible.

Optionally, the spring clips 38, 40 are cut from a flat section of metallic stock material. Suitable metallic materials include shape memory alloys such as alloys of nitinol and beta-titanium. The clips 38, 40 may be cut from the stock material using a stamping, die cutting, chemical etching, EDM (electrical discharge machining), laser cutting or water jet cutting process. As another option, the clips 38, 40 could be formed and then heat treated to set their shapes.

As presently preferred, the clips 38, 40 are made from flat annealed superelastic material (such as nitinol) having a pickled surface. Preferred nitinol materials have a nickel content of 55.97% by weight $A_f$ of 10°±5° C. The nitinol is cold worked to 37.5% and has a thickness in the range of about 0.012 in. (0.3 mm) to about 0.016 in. (0.4 mm). The clips 38, 40 are first cut in a rough cutting EDM process, then cut along their edges for an additional one or more times using an EDM process in order to smooth the edges. Alternatively, a laser cutting process or chemical etching process could be used to make the clips 38, 40. Preferably, the clips 38, 40 are constructed so that the longitudinal direction of the clip material, or the principal direction of grain flow of the clip material, is substantially parallel to the direction of extension of the first and second sections 42, 44 (i.e. a generally buccolabial direction).

Subsequent to the EDM, laser cutting or chemical etching process, the clips 38, 40 are tumbled in order to further round their edges. An example of a suitable tumbling machine is model LC-600-2+2 from Richwood Industries. Using a small barrel, and a machine speed of 200 rpm, the clips are tumbled for about 2 hours in 500 cc of water and tumbling media. An example of suitable tumbling media is a mixture of 500 cc of ceramic media (shaped ACC, type M, size 3/16×3/8 (4.7 mm×9.5 mm), 25 cc of white alumina powder no. 40, and 25 cc of soap powder compound no. 43, all from Richwood Industries. The tumbled clips are then polished for one-half hour in an ultrasonic screen barrel in a tank of solution. An example of a suitable solution is 3 liters of deionized water, 3 liters of pickling solution and 0.6 liter of hydrogen peroxide. A suitable pickling solution is No. TI121 Pickling Solution from Aya International of Los Angeles, Calif.

Advantageously, the shape of the clip 38 as shown in FIGS. 4 and 5 reduces maximum strain and stress during opening and closing movements so that the expected useful life of the clip 38 is increased. In particular, the decrease in width of the first and second sections 42, 44 as the arm portions 60, 62 respectively are approached serves to reduce maximum strain to significantly lower levels. Preferably, this width is a dimension that is determined along an occlusal-gingival reference axis and the decrease in width is carried out gradually as the arm portions 60, 62 are approached. The provision of the recess 54 also helps to reduce maximum strain and stress when the clip 38 is opened during assembly of the appliance 20. The provision of the notches 58 helps to safely provide a gradual decrease in width while enabling the recess 54 to be smaller than the region 46 in directions along an occlusal-gingival reference axis. As an example, it was found in one analysis that careful selection of the overall shape of the perimeter of the first and second sections 42, 44 helped to reduce maximum strain from 0.116 to 0.067 and maximum stress from 98,700 psi to 75,200 psi.

Optionally, and as shown in the drawings, the third section 48 extends in a direction other than 90 degrees from the direction of extension of the first and second sections 42, 44 when the clip 38 is in its normally relaxed orientation. Additionally, a hypothetical reference plane resting on an outer edge of the third section 48 extends in a direction other than 90 degrees from the direction of extension of the first and second sections 42, 44 when the clip 38 is in its normally relaxed configuration. Such construction is particularly useful for brackets having what is known as "torque-in-base" as shown in FIGS. 1–3.

For example, and with reference to FIG. 2, the torque-in-base appliance has an archwire slot with a lingual wall that is oriented at an acute angle relative to the overall orientation of the base 22. The orientation of the third section 48 helps ensure that the corners 50, 52 firmly bear against the buccolabial side of the base 22 once the clip 38 is assembled to remaining components of the appliance 20. For brackets with a zero degree torque, the reference plane mentioned above extends at a substantially 90 degree direction from the direction of the first and second sections 42, 44, but in those instances it is also preferred that the corners 50, 52 firmly bear against the buccolabial side of the base 22.

The body 24 may be made by any suitable manufacturing process such as machining or injection molding (including metal injection molding). Suitable materials for the body 24 include stainless steel nos. 17-4 PH, although other materials are also possible. Preferably, the tumbling and heat treating operations are carried out after the body 24 is fabricated.

Figure 6:
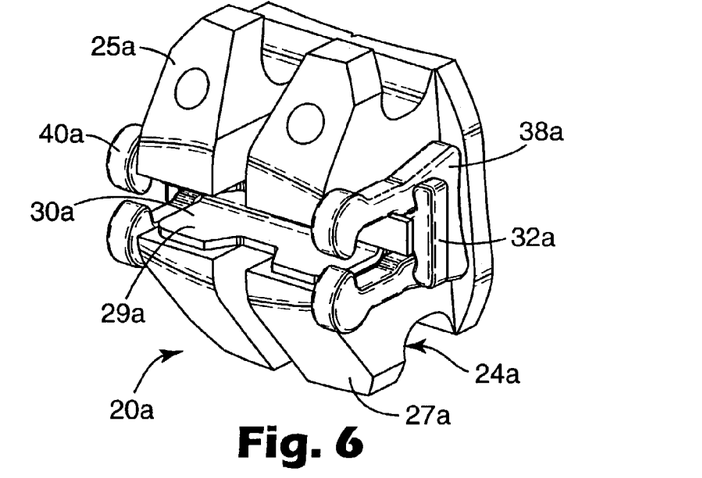
FIG. 6 is a perspective view of an orthodontic appliance having a latch in accordance with yet another embodiment of the present invention.
Figure 7:
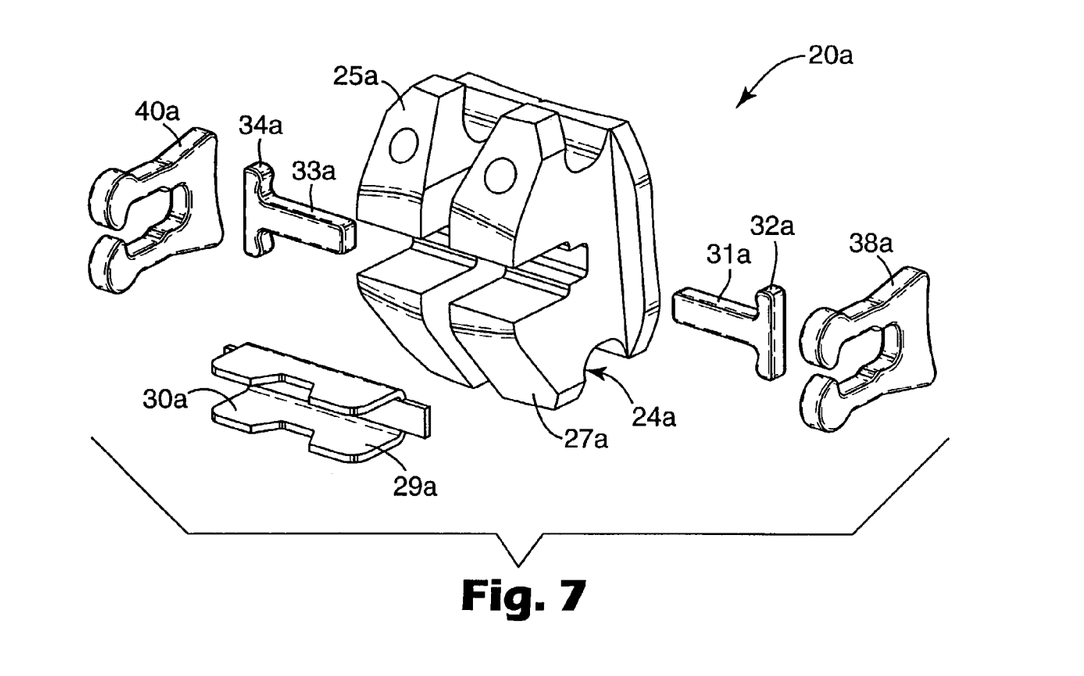
FIG. 7 is an exploded perspective view of the appliance shown in FIG. 6.

An orthodontic appliance 20a that is constructed in accordance with another embodiment of the invention is illustrated in FIGS. 6 and 7. The appliance 20a includes an aesthetic ceramic body 24a that is preferably integrally connected to an aesthetic ceramic base 22a. The body 24a includes mesial and distal body sections 25a, 27a respectively and is somewhat similar to the appliances described in U.S. Pat. Nos. 5,439,379 and 5,366,372, both of which are expressly incorporated by reference herein. The appliance 20a also includes a metallic archwire slot liner 29a that defines an archwire slot 30a.

Examples of suitable materials and methods for constructing the archwire slot liner 29a, as well as examples of suitable methods for attaching the archwire slot liner 29a to the body sections 25a, 27a are described in U.S. Pat. Nos. 5,358,402 and 5,380,196, both of which are expressly incorporated by reference herein. In addition, a mesial and distal elongated support 31a, 33a are fixed to a lingual side of the archwire slot liner 29a. Preferably, the supports 31a, 33a are made of a metallic material that is brazed or welded to the archwire slot liner 29a.

The mesial support 31a is integrally connected to a mesial flange 32a and the distal support 33a is integrally connected to a distal flange 34a. The supports 31a, 33a, together with the flanges 32a, 34a, serve to hold clips 38a, 40a in place. The clips 38a, 40a comprise a latch 36a for releasably retaining an archwire in the archwire slot 30a.

To assemble the appliance 20a, the clips 38a, 40a are moved relative to the supports 31a, 33a until such time as the supports 31a, 33a are received recesses of the clips 38a,

40a. Next, the combination of the archwire slot liner 29a, the supports 31a, 33a and the clips 38a, 40a is set in place on the body 24a such that the archwire slot liner 29a is received in a mesial-distal channel that extends through the body sections 25a, 27a. Once this assembly is in place, the archwire slot liner 29a and optionally also the supports 31a, 33a are fixed to the ceramic body 24a, preferably according to the methods described in U.S. Pat. Nos. 5,358,402 and 5,380,196 as mentioned above. Alternatively, the supports 31a, 33a may be fixed to the liner 29a before the liner 29a is secured to the body 24a.

In other respects, the clips 38a, 40a are the same as the clips 38 and 40 set out above. Accordingly, a detailed description of the construction of the clips 38a, 40a need not be repeated.

The examples described above are intended to exemplify the various aspects and benefits of the invention. However, those skilled in the art may recognize that a number of variations and additions to the appliances described above may be made without departing from the spirit of the invention. Accordingly, the invention should not be deemed limited to the specific embodiments set out above in detail, but instead only by a fair scope of the claims that follow along with their equivalents.

The invention claimed is:

1. An orthodontic appliance comprising a base for bonding the appliance to a tooth, a body extending from the base, an archwire slot extending across the body in a generally mesial-distal direction, a support, and a latch connected to the body for releasably retaining an archwire in the archwire slot, the latch including a clip comprising:
   a first section;
   a second section opposed to the first section, the first section and the second section being spaced apart from each other to present a region for receiving an archwire;
   a third section extending in a certain direction and interconnecting the first section and the second section;
   a first arm portion connected to the first section remote from the third section; and
   a second arm portion connected to the second section remote from the third section, wherein the first section and the second section are movable toward and away from each other for enabling the arm portions to retain and release an archwire in the region between the first section and the second section respectively, wherein the clip includes a recess communicating with the archwire-receiving region, wherein the support is received in the recess, and wherein the first section decreases in width next to the region as the first arm portion is approached and the second section decreases in width next to the region as the second arm portion is approached.

2. A clip for releasably retaining an archwire in an archwire slot of an orthodontic appliance, the clip comprising:
   a first section;
   a second section opposed to the first section, the first section and the second section being spaced apart from each other to present a region for receiving an archwire;
   a third section extending in a certain direction and interconnecting the first section and the second section;
   a first arm portion connected to the first section remote from the third section; and
   a second arm portion connected to the second section remote from the third section, wherein the first section and the second section are movable toward and away from each other for enabling the arm portions to retain and release an archwire in the region between the first section and the second section respectively, and wherein the first section decreases in width as the first arm portion is approached and the second section decreases in width as the second arm portion is approached, wherein the third section has outer corners that extend beyond the first section and the second section in said certain direction.

3. An orthodontic appliance according to claim 1 wherein the recess is smaller than the region in directions parallel to said certain direction.

4. An orthodontic appliance according to claim 1 wherein the first section and the second section extend in generally parallel directions, wherein the third section includes an outer edge remote from the first section and the second section, and wherein a reference plane resting on the outer edge extends at an angle of other than 90 degrees relative to the direction of extension of the first section and the second section.

5. An orthodontic appliance according to claim 1 wherein the clip is made from a shape memory material having superelastic properties.

6. An orthodontic appliance according to claim 1 wherein the third section has an outer edge with a concave configuration.

7. An orthodontic appliance according to claim 1 wherein the first section and the second section are essentially mirror images.

8. An orthodontic appliance according to claim 1 wherein the width is determined in a generally occlusal-gingival direction.

9. An orthodontic appliance according to claim 1 wherein the recess is smaller than the region in directions parallel to said certain direction, and wherein the decrease in width of the first section and the second section is present in locations adjacent the intersection of the recess and the region.

10. An orthodontic appliance according to claim 1 wherein the first arm portion has an outer corner that extends beyond the first section in said certain direction, and wherein the second arm portion has an outer corner that extends beyond the second section in the certain direction.

11. An orthodontic appliance according to claim 10 wherein the body is made of a ceramic material.

12. An orthodontic appliance according to claim 10 wherein the body is made of a metallic material.

13. An orthodontic appliance according to claim 10 wherein the body is made of a plastic material.

14. An orthodontic appliance according to claim 10 wherein the appliance includes a mesial clip adjacent a mesial side of the body and a distal clip adjacent a distal side of the body.

15. An orthodontic appliance comprising a base for bonding the appliance to a tooth, a body extending from the base, an archwire slot extending across the body in a generally mesial-distal direction, a support, and a latch connected to the body for releasably retaining an archwire in the archwire slot, the latch including at least one clip comprising:
   a first section;
   a second section opposed to the first section, the first section and the second section being spaced apart from each other to present a region for receiving an archwire;
   a third section extending in a certain direction and interconnecting the first section and the second section;
   a first arm portion connected to the first section remote from the third section;
   a second arm portion connected to the second section remote from the third section; wherein the arm portions are movable toward and away from each other for retaining and releasing an archwire in the region between the first section and the second section respectively, and a recess adjacent the third section and communicating with the archwire-receiving region, wherein the support extends through the recess, the recess being smaller than the region in areas adjacent the region in directions parallel to said certain direction.

16. An orthodontic appliance according to claim 15 wherein the first arm portion has an outer corner that extends beyond the first section in said certain direction, and wherein the second arm portion has an outer corner that extends beyond the second section in the certain direction.

17. An orthodontic appliance according to claim 15 wherein the first section and the second section extend in generally parallel directions, wherein the third section includes an outer edge remote from the first section and the second section, and wherein a reference plane resting on the outer edge extends at an angle of other than 90 degrees relative to the direction of extension of the first section and the second section.

18. An orthodontic appliance according to claim 15 wherein the clip is made from a shape memory material having superelastic properties.

19. An orthodontic appliance according to claim 15 wherein the third section has an outer edge with a concave configuration.

20. An orthodontic appliance according to claim 15 wherein the first section and the second section are essentially mirror images.

21. An orthodontic appliance according to claim 15 wherein the first section and the second section extend in generally parallel directions, wherein the third section includes an outer edge remote from the first section and the second section, and wherein a reference plane resting on the outer edge extends at an angle of other than 90 degrees relative to the direction of extension of the first section and the second section.

22. An orthodontic appliance according to claim 15 wherein the support is received in the recess.

23. An orthodontic appliance according to claim 15 wherein the body is made of a ceramic material.

24. An orthodontic appliance according to claim 15 wherein the body is made of a metallic material.

25. An orthodontic appliance according to claim 15 wherein the body is made of a plastic material.

26. An orthodontic appliance according to claim 15 wherein the latch includes a mesial clip adjacent a mesial side of the body and a distal clip adjacent a distal side of the body.

* * * * *